(12) United States Patent
Chen et al.

(10) Patent No.: US 9,872,827 B2
(45) Date of Patent: Jan. 23, 2018

(54) CROSS-LINKED SODIUM HYALURONATE GEL FOR TISSUE FILLER FOR PLASTIC SURGERY AND PREPARATION METHOD THEREOF

(71) Applicant: Hangzhou Gallop Biological Products Co., Ltd., Zhejiang (CN)

(72) Inventors: Xuejun Chen, Zhejiang (CN); Xiaobin Zhao, Zhejiang (CN); Yitao Zou, Zhejiang (CN)

(73) Assignee: Hangzhou Gallop Biological Products Co., Ltd., Hangzhou (CN)

( * ) Notice: Subject to any disclaimer, the term of this patent is extended or adjusted under 35 U.S.C. 154(b) by 60 days.

(21) Appl. No.: 14/432,405

(22) PCT Filed: Jul. 26, 2013

(86) PCT No.: PCT/CN2013/080217
§ 371 (c)(1),
(2) Date: Aug. 6, 2015

(87) PCT Pub. No.: WO2014/048168
PCT Pub. Date: Apr. 3, 2014

(65) Prior Publication Data
US 2015/0328123 A1    Nov. 19, 2015

(30) Foreign Application Priority Data

Sep. 29, 2012 (CN) .......................... 2012 1 0372786

(51) Int. Cl.
*A61K 8/73* (2006.01)
*A61Q 19/00* (2006.01)
*A61Q 19/08* (2006.01)
*A61K 8/04* (2006.01)
*C08J 3/075* (2006.01)
*C08L 71/08* (2006.01)
*A61L 27/20* (2006.01)
*A61L 27/52* (2006.01)
*C08B 37/08* (2006.01)
*C08L 63/00* (2006.01)

(52) U.S. Cl.
CPC .............. *A61K 8/735* (2013.01); *A61K 8/042* (2013.01); *A61L 27/20* (2013.01); *A61L 27/52* (2013.01); *A61Q 19/00* (2013.01); *A61Q 19/08* (2013.01); *C08B 37/0072* (2013.01); *C08J 3/075* (2013.01); *C08L 63/00* (2013.01); *C08L 71/08* (2013.01); *A61K 2800/91* (2013.01); *A61L 2400/06* (2013.01); *A61L 2430/02* (2013.01); *A61L 2430/06* (2013.01); *A61L 2430/24* (2013.01); *C08J 2305/08* (2013.01)

(58) Field of Classification Search
CPC .... A61K 8/735; A61K 8/042; A61K 2800/91; A61Q 19/00; A61Q 19/08; A61L 27/20; C08L 5/08; C08L 63/00
USPC .......................................................... 514/54
See application file for complete search history.

(56) References Cited

U.S. PATENT DOCUMENTS

| | | | | |
|---|---|---|---|---|
| 4,713,448 A | * | 12/1987 | Balazs | ................ C08B 37/0072 435/267 |
| 6,231,614 B1 | * | 5/2001 | Yang | ..................... A61L 24/001 623/23.72 |
| 2002/0091251 A1 | * | 7/2002 | Zhao | ....................... A61L 27/20 536/53 |
| 2003/0148995 A1 | | 8/2003 | Piron et al. | |
| 2010/0316683 A1 | * | 12/2010 | Piron | ....................... A61K 8/02 424/401 |
| 2013/0172288 A1 | * | 7/2013 | Bon Betemps | ........ C07H 15/12 514/54 |

FOREIGN PATENT DOCUMENTS

| | | |
|---|---|---|
| CN | 1342170 A | 3/2002 |
| CN | 1829743 A | 9/2006 |
| CN | 102863631 A | 1/2013 |

OTHER PUBLICATIONS

International Search Report dated Oct. 31, 2013, issued by the State Intellectual Property Office of the People's Republic of China in corresponding International Application No. PCT/CN2013/080217, with English translation (9 pages).

Written Opinion of the International Searching Authority dated Oct. 31, 2013, in corresponding International Application No. PCT/CN2013/080217, with English translation (13 pages).

(Continued)

*Primary Examiner* — Yih-Horng Shiao
(74) *Attorney, Agent, or Firm* — Liang Legal Group, PLLC

(57) ABSTRACT

The present invention relates to a cross-linked sodium hyaluronate gel for tissue filler for plastic surgery and the preparation method thereof. The alkaline solution of sodium hyaluronate reacts with the long chain alkane containing epoxy group and the cross-linking agent containing epoxy group for 2~5 hours at 35° C.~50° C. to produce cross-linked sodium hyaluronate, then washed, gelled and sterilized, to prepare the gel. Among which, the molar ratio of sodium hyaluronate:cross-linking agent containing epoxy group:long chain alkane containing epoxy group is 10:4~1:1~4; the number of carbon atoms of the said long chain alkane containing epoxy group is 6 to 18. The gel prepared in the present invention can, on one hand, effectively enhance the resistance to enzymolysis to become more stable, and on the other hand, maintain the excellent biocompatibility of sodium hyaluronate without affecting its injectability.

2 Claims, 6 Drawing Sheets

(56) References Cited

OTHER PUBLICATIONS

PCT International Preliminary Report on Patentability dated Mar. 31, 2015, issued by the International Bureau of WIPO in corresponding International Application No. PCT/CN2013/080217, with English translation (15 pages).

\* cited by examiner

CROSS-LINKED SODIUM HYALURONATE GEL FOR TISSUE FILLER FOR PLASTIC SURGERY AND PREPARATION METHOD THEREOF

TECHNICAL FIELD

The present invention relates to a cross-linked sodium hyaluronate gel for tissue filler for plastic surgery and its preparation method thereof.

BACKGROUND ART

Hyaluronic acid (hereinafter referred to as HA) or its sodium salt is a kind of natural polymer mucopolysaccharide substance, which is widely distributed in mammalian connective tissue, comb and the capsules of *Streptococcus*. Since having no specificity of species and organs, the HA gel prepared from HA has good body compatibility when transplanted or injected to the body as a filler, having the functions of anti-wrinkling, breast enlargement and padding but without any side effects on human body. Therefore, it is widely used in medicine and beauty. The skill fillers made from HA or its sodium salts are most popular in the plastic surgery. These tissue fillers, similar to collagen, have a longer efficacy and lower risk of allergic reactions. However, HA or its sodium salt is easy to degrade in vivo due to the function of HA hydrolase and free radicals, thus, its in vivo retention time is short. To enhance in vivo retention time of HA or its sodium salt, usually HA or its sodium salt is crosslinked, so that the hydroxyl group in the polymer chain of HA or its sodium salt is chemically bonded with the cross-linking agent to prepare the cross-linked HA or its sodium salt gel. In order not to affect the biocompatibility of the gel, the concentration of cross-linking agent should not be too high. But when the consumption of cross-linking agent is low, the resulting gel derivative has a low resistance to the in vivo hydrolysis, the in vivo retention time is short, usually about 1-6 months. When the consumption of cross-linking agent is excessive, the in vivo retention time is extended, but the viscosity is high and the gel hardness is increased, not easy to pass the needles of 30G even 27G with a decreased injectability. In addition, when the consumption of cross-linking agent is high, excessive cross-linking agent will remain in the product, difficult to clean and purify, which makes the cytotoxicity of the cross-linked HA or its sodium salt gel greater and easy to produce side effect on human body. The cross-linking reaction of the existing HA or its sodium salt is performed in a homogeneous aqueous alkaline solution, which can enhance the anti-biodegradability by improving the degree of cross-linking and extend the in vivo retention time of skin filler. Thus, it will, on the one hand, undermine the biocompatibility of cross-linked HA or its sodium salt gel, and on the other hand, reduce the viscoelasticity of gel products, increase the hardness and decrease the injectability.

SUMMARY OF THE INVENTION

The first object of the present invention is to provide a cross-linked sodium hyaluronate gel for tissue filler for plastic surgery that can effectively enhance the resistance to enzymolysis and maintain the excellent biocompatibility of sodium hyaluronate.

The technical scheme that realizes the first object of the invention is: A cross-linked sodium hyaluronate gel for tissue filler for plastic surgery, wherein the alkaline solution of sodium hyaluronate reacts with the long-chain alkane containing epoxy group and the cross-linking agent containing epoxy group for 2-5 hours at 35° C.-50° C. to produce cross-linked sodium hyaluronate, then washed, gelled and sterilized, to prepare the gel. Among which, the weight ratio of sodium hyaluronate:cross-linking agent containing epoxy group:long-chain alkane containing epoxy group is 10:4-1:1-4.

The number of carbon atoms of said long-chain alkane containing epoxy group is 6 to 18;

The said cross-linking agent containing epoxy group is one of the following: 1,4-butanediol diglycidyl ether, polyethylene glycol diglycidyl ether with molecular weight of 500~6,000, 1,2,7,8-diepoxyoctane and 1,2,3,4-diepoxybutane;

The said alkaline solution of sodium hyaluronate is prepared by the dry powder of sodium hyaluronate dissolved in the mixture of 0.2~0.5M aqueous sodium hydroxide solution and dimethyl sulfoxide, of which, the concentration of sodium hyaluronate is 4 wt %-8 wt %; and the volume ratio of 0.2~0.5M aqueous sodium hydroxide solution to the dimethyl sulfoxide is 10:7~1.

The chemical structure of above said cross-linked sodium hyaluronate gel includes the chemically bonded hydrophobic groups with the self-adhesive self-aggregation function, and the number of carbon atoms in the hydrophobic group is 6~18.

The second object of the present invention is to provide a method for preparing cross-linked sodium hyaluronate gel for tissue filler for plastic surgery that can effectively enhance the resistance to enzymolysis and maintain the excellent biocompatibility of sodium hyaluronate. The procedures of this method are easy to operate, to maintain a stable product quality.

The technical scheme that realizes the second object of the invention is: a method for preparing the cross-linked sodium hyaluronate gel for tissue filler for plastic surgery, comprising the following steps:

①The dry powder of sodium hyaluronate is dissolved in the mixture of 0.2~0.5M aqueous sodium hydroxide solution and dimethyl sulfoxide to get the alkaline solution of sodium hyaluronate, and then added with long-chain alkane containing epoxy group and the cross-linking agent containing epoxy group, heated to 35° C.~50° C. at the stirring state and kept warm 2~5 hours, cooled down to the room temperature; then add dropwise acetone to form a solid-liquid mixing material while stirring, add hydrochloric acid to adjust the pH value of solid-liquid mixing material to 6.5~7.4. After the mixture is filtered, the resulting solid material is washed 3~5 times using isopropanol and acetone, respectively, and then vacuum dried until the content of the volatile matter lower than 2 ppm. The resulting dry white powder is the cross-linked sodium hyaluronate powder;

Of which, the weight ratio of sodium hyaluronate:cross-linking agent containing epoxy group and long-chain alkane containing epoxy group is 10:4-1:1-4; the number of carbon atoms in the long-chain alkane containing epoxy group is 6~18; the volume ratio of 0.2~0.5M sodium hydroxide solution to dimethyl sulfoxide is 10:7~1; the concentration of sodium hyaluronate is 4 wt %-8 wt % in the sodium hyaluronate alkaline solution; the volume ratio of sodium hydroxide solution to acetone added dropwise is 1:4~2:3; the average molecular weight of sodium hyaluronate is 500,000~2,000,000; the said cross-linking agent containing epoxy group is one of the following: 1,4-butanediol diglycidyl ether, polyethylene glycol diglycidyl ether with molecular weight of 500~6,000, 1,2,7,8-diepoxyoctane and 1,2,3,4-diepoxybutane;

② Add water for injection to the cross-linked sodium hyaluronate powder obtained in step ① to form the cross-linked sodium hyaluronate gel; collect the gel particles and add the water for injection, stir and wash it 2~5 hours at 15° C.~35° C. Filter the water for injection, collect the gel particles, and then wash with water for injection. After repeated washing 4~5 times according to the above procedures, collect the gel particle which is the cross-linked sodium hyaluronate gel;

③ Add isotonic saline to the gel particles collected in step ②; after washing 2~5 hours at 15° C.~35° C. while stirring, filter the isotonic saline, collect the gel particles, and wash with isotonic saline. After repeated washing 4~5 times according to the above procedures, collect the gel with average particle size of 150 μm~350 μm through screen sieving;

④ Fill the gel particles collected in step ③ into a pre-sterilized disposable syringe, sterilize it by steam at 121° C.~125 for 15~25 min, to get the cross-linked sodium hyaluronate gel for tissue filler for plastic surgery.

In the above said method of preparing crosslinked sodium hyaluronate gel, the chemical structure of the obtained cross-linked sodium hyaluronate gel contains the chemically bonded hydrophobic groups with the self-adhesive self-aggregation function, and the number of carbon atoms in the hydrophobic group is 6~18.

The technical effects of the present invention are: In the technical scheme of the present invention, cross-linking agent containing epoxy group is used, such as cross-linking between 1,4-butanediol diglycidyl ether and sodium hyaluronate, while introducing appropriate amount of long-chain alkane containing epoxy group (the number of carbon atoms in the long chain alkane is 6~18), since the long chain alkane is a hydrophobic group, it becomes a part of gel network molecular structure of cross-linked sodium hyaluronate, which adjusts the hydrophilicity of cross-linked sodium hyaluronate gel, avoids the entry of enzyme, and thus resulting in degradation of cross-linked sodium hyaluronate and prolonging its in vivo retention time, i.e., the filler can maintain a longer effect on tissue volume filling, in addition, the introduction of long-chain alkane generates self-adhesive self-aggregation function through strong hydrophobic association, and will then form a lot of physical clusters in cross-linked sodium hyaluronate gel, which thus can achieve the effect of increased resistance to enzymolysis, and would not affect the biocompatibility and other physical properties of the gel, reaching the same anti-enzymolysis stability under the condition of high degree of cross-linking, even a higher stability. Compared to the gel featuring in the same degree of cross-linking, because the sodium hyaluronate gel in the present invention owns the above self-adhesive self-aggregation function, which can make in vitro anti-enzymolysis stability of sodium hyaluronate gel in the present invention increased by 2 to 3 times, the residence time in the body is greatly extended, and therefore, the long-acting stability of the gel is improved. In the present invention, it is found that, since the degree of swelling of the gel is not decreased due to the introduction of hydrophobic chains, and therefore, the flexibility of the gel can be maintained, requiring no additional lubricant, to pass through a 30G injection needle (as shown in Table 2).

Figure 3:
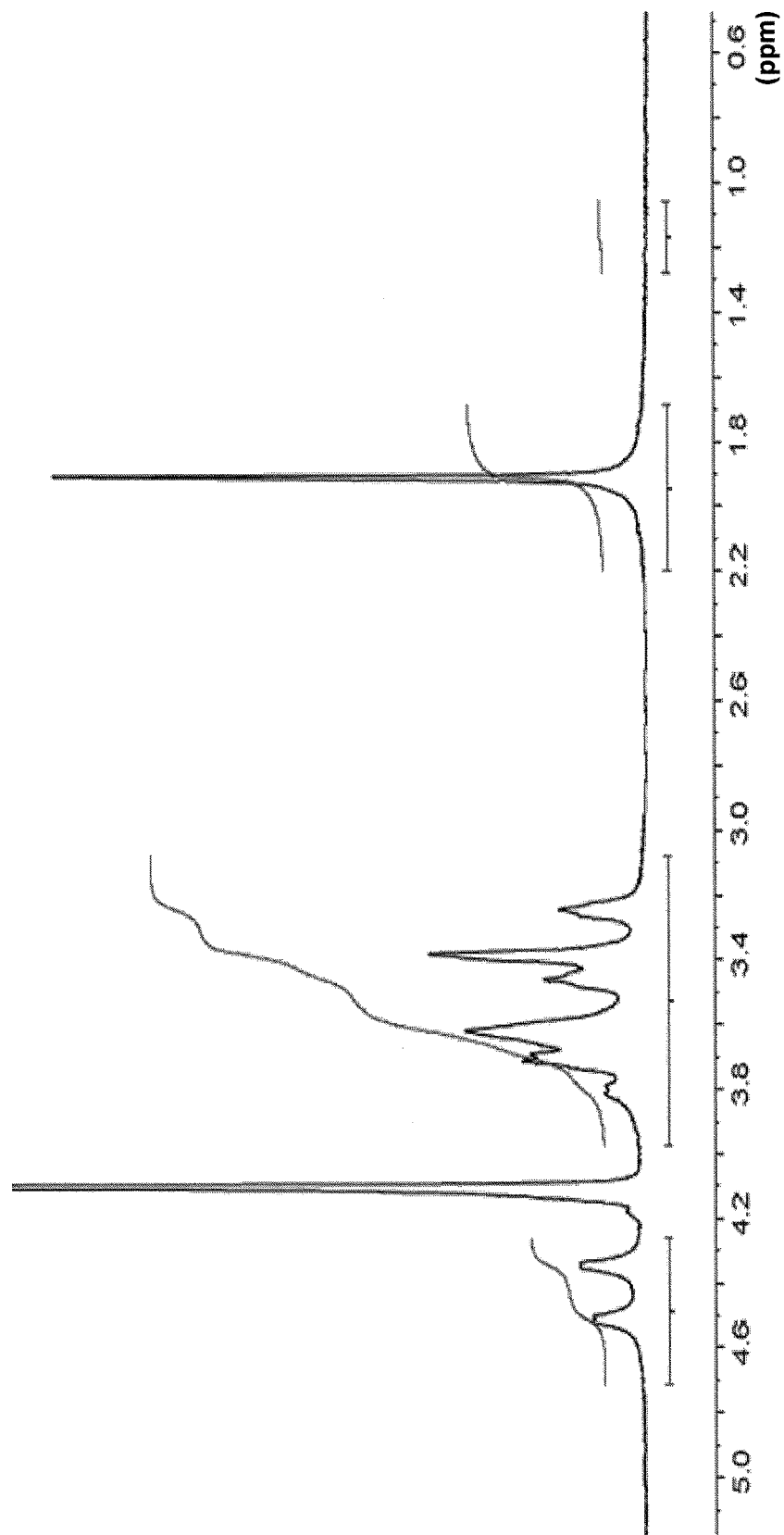
Figure 4:
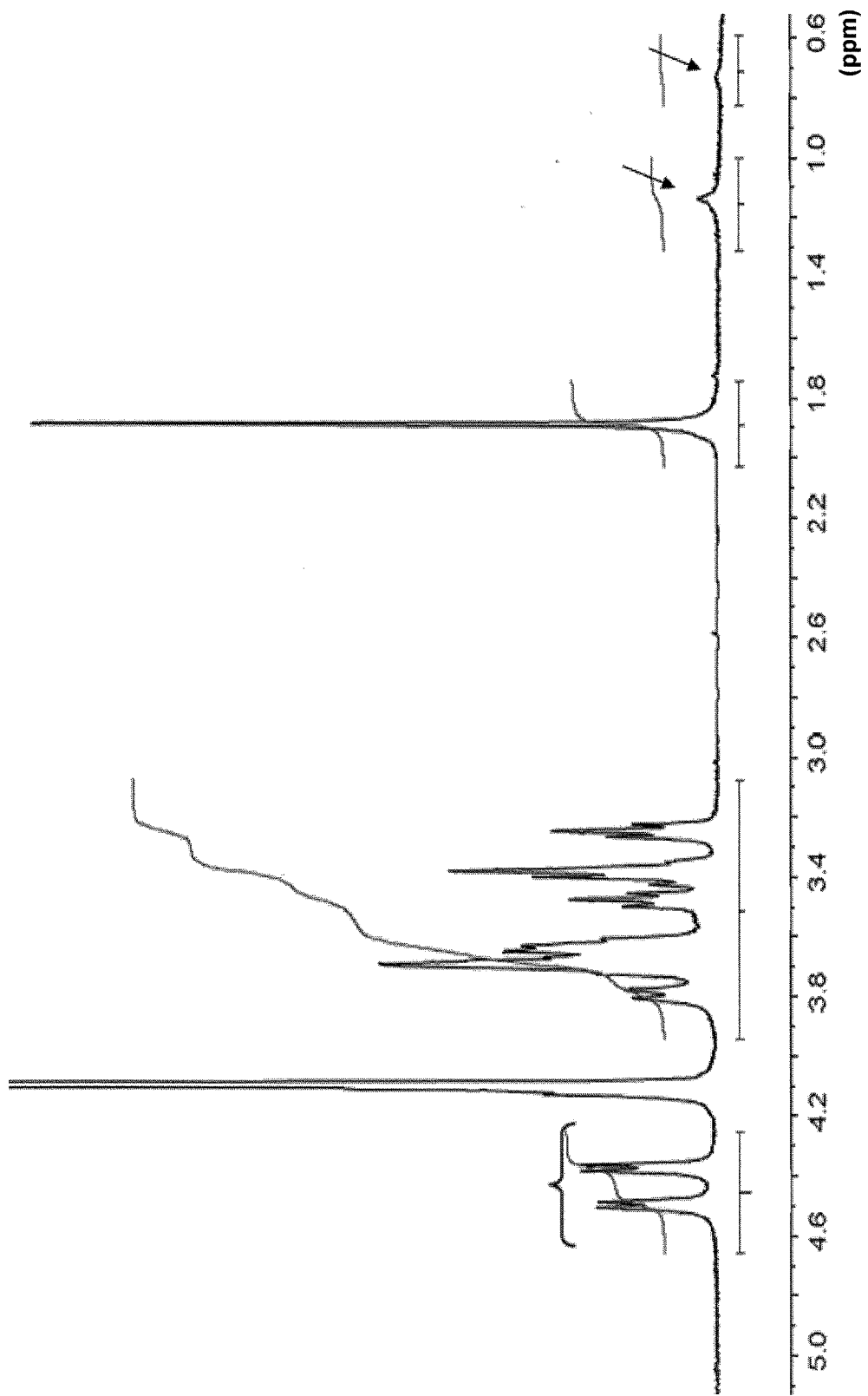
Figure 5:
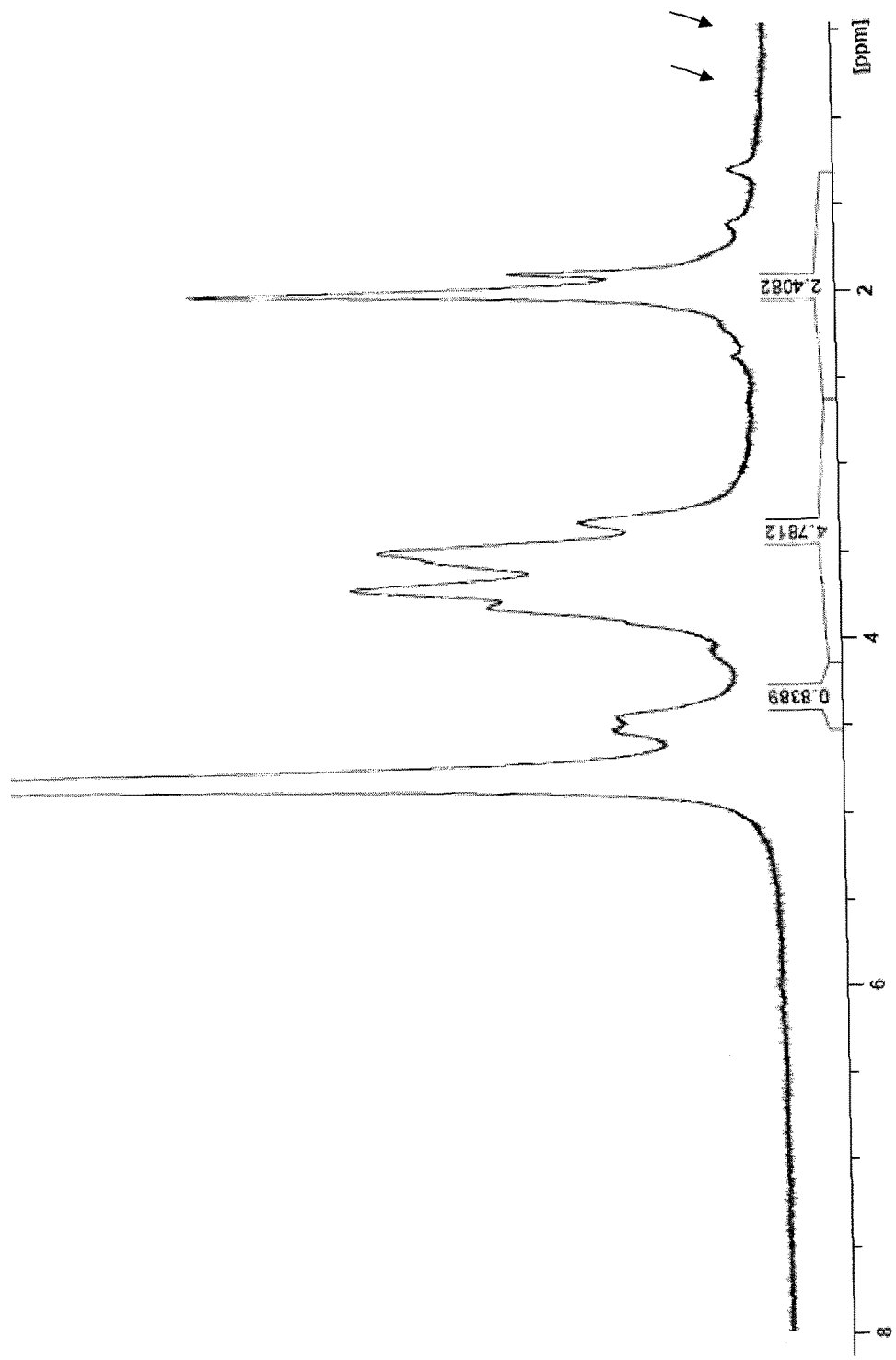
Figure 6:
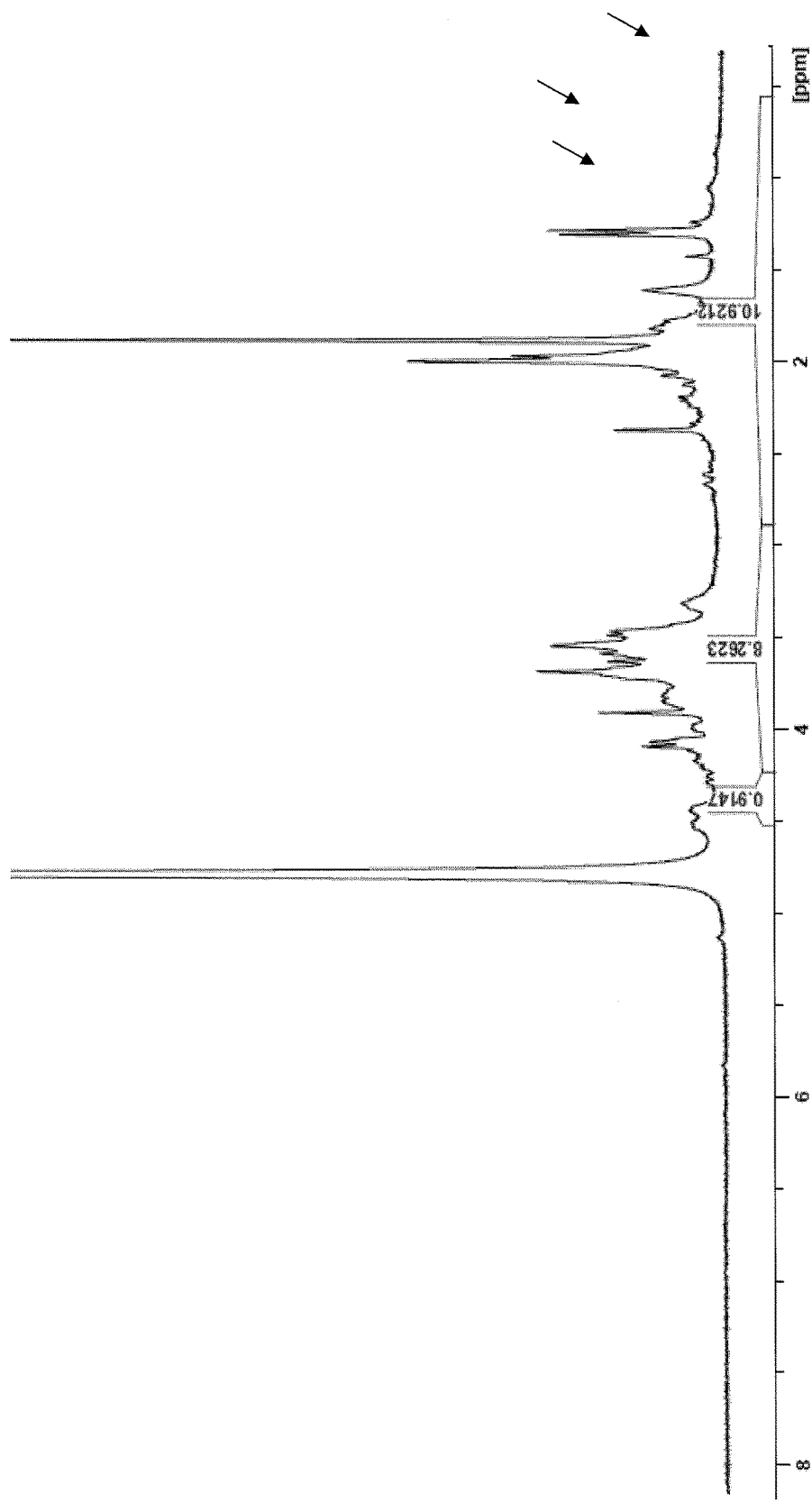

Of which, 1 is a FT-IR spectrum of sodium hyaluronate used as a raw material in the present invention; 2 is a FT-IR spectrum of cross-linked sodium hyaluronate gel in the present invention;

FIG. 3 is the standard $^1$H-NMR spectrum of sodium hyaluronate used as a raw material in the present invention;

FIG. 4 is the $^1$H-NMR spectrum of sodium hyaluronate after treated alone using the long-chain alkane containing epoxy group in the present invention;

FIG. 5 is the $^1$H-NMR spectrum of sodium hyaluronate after cross-linked alone using 1,4-butanediol diglycidyl ether in the present invention;

FIG. 6 is the $^1$H-NMR spectrum of cross-linked sodium hyaluronate gel after treated using long-chain alkane containing epoxy group and 1,4-butanediol diglycidyl ether (cross-linking agent) in the present invention.

DETAILED DESCRIPTIONS OF THE PREFERRED EMBODIMENTS

The invention is described herein in connection with drawings and certain specific embodiments. However, it is not to be construed as limiting the scope of the invention.

Raw materials used in the examples are commercially available pharmaceutical grade products unless otherwise noted, and can be available through commercial channels.

Figure 1:
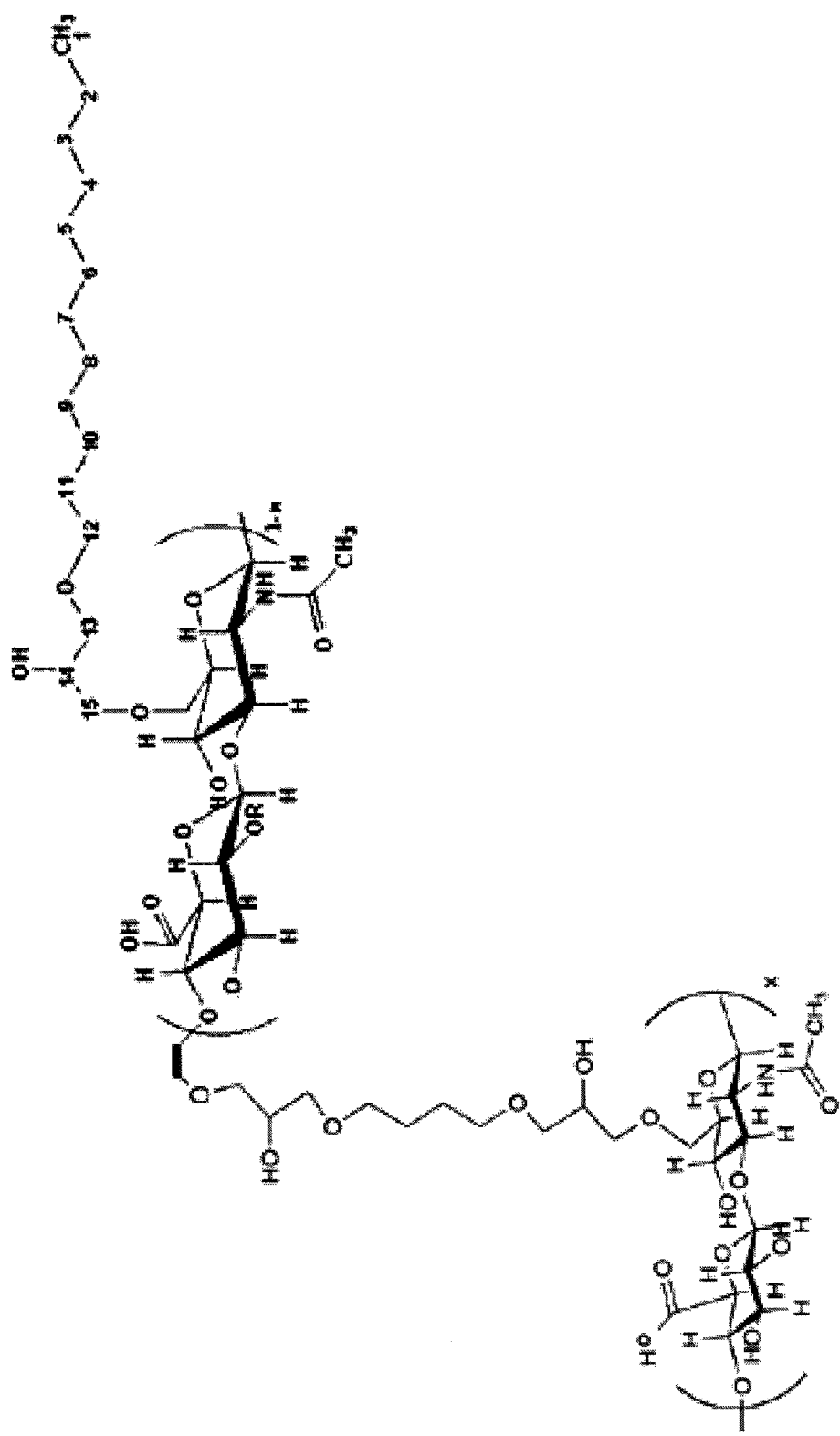
FIG. 1 is the chemical structure schematic of the cross-linked sodium hyaluronate gel in the present invention.

Example 1: Preparation of Cross-Linked Sodium Hyaluronate Gel for Tissue Filler for Plastic Surgery Specific steps are as follows:

① After 10 g of dry powder of sodium hyaluronate (average molecular weight of 2,000,000) is dissolved in a mixture of 200 ml of 0.5M sodium hydroxide solution and 50 ml of dimethyl sulfoxide to get alkaline solution of sodium hyaluronate, and then added with 0.5 ml of long-chain alkane containing epoxy group-1,2-epoxy dodecane (molecular weight: 184.32, purity: 98%, Sigma) and 1 ml cross-linking agent containing epoxy group-1,4-butanediol diglycidyl ether (molecular weight: 202.25, purity: 98%, Sigma), heated to 40° C. at the stirring state and kept warm 5 hours, cooled down to the room temperature (15° C.~30° C.); then add dropwise acetone until appearing white powder and forming a solid-liquid mixing material while stirring (800 ml of volume of acetone added), add 5M hydrochloric acid to adjust the pH value of solid-liquid mixing material to 7. After the mixture is filtered, the resulting solid powder is washed 3 times using isopropanol and 5 times using acetone, respectively (100 ml of isopropanol and 100 ml of acetone, each time), and then vacuum dried until the content of the volatile matter lower than 2 ppm. The resulting dry white powder is the cross-linked sodium hyaluronate powder. Its chemical structural formula is shown in FIG. 1;

Of which, the weight ratio of sodium hyaluronate:1,4-butanediol diglycidyl ether:1,2-epoxy dodecane is 10:2:1; the number of carbon atoms in the long-chain alkane containing epoxy group is 12; the volume ratio of 0.2~0.5M sodium hyaluronate solution to dimethyl sulfoxide is 4:1; the concentration of sodium hyaluronate is 4.0 wt % in the sodium hyaluronate solution; the volume ratio of sodium hydroxide solution to acetone added dropwise is 1:4;

② Add 1 L of water for injection to the cross-linked sodium hyaluronate powder obtained in step ① to form the cross-linked sodium hyaluronate gel after swelling 8 hours at 25° C., collect the gel particles and add 1 L of water for injection, stir and wash it 2 hours at 25° C. Filter the water for injection, collect the gel particles, and then wash with water for injection. After repeated washing 4 times according to the above procedures, collect the gel particle which is the cross-linked sodium hyaluronate gel;

③ Add 500 ml of isotonic saline to the gel particles collected in step ②; after washing 2 hours at 25° C. while stirring, filter the isotonic saline, collect the gel particles, and wash with isotonic saline. After repeated washing 4 times according to the above procedures, collect the gel particles with average particle size of 250 μm through screen sieving;

④ Fill the gel particles collected in step ④ into a pre-sterilized disposable syringe, sterilize it 25 min at 121° C. steam, to get the cross-linked sodium hyaluronate gel for tissue filler for plastic surgery.

Example 2-Example 7

Preparation of Cross-Linked Sodium Hyaluronate Gel for Tissue Filler for Plastic Surgery Specific steps are basically the same as those in the Example 1, with the differences as follows: in the step ① in example 1, the feeding quantity and the weight ratio of sodium hyaluronate:1,4-butanediol diglycidyl ether:1,2-epoxy dodecane are as shown in Table 1, to get the cross-linked sodium hyaluronate gel with different consumption of 1,4-butanediol diglycidyl ether and 1,2-epoxy dodecane.

would also increase, but under a certain proportion (example 7), the hardness of gel increases, and the injectability decreases. The injectability must be increased by the lubricant; in addition, the cytotoxicity increases. In the present invention, by introducing the long-chain alkane containing epoxy group (in examples 1, 5, 6), the HA hydrophilicity will not be affected, and the degree of swelling of the gel does not fall, but the resistance to enzymolysis would be increased; meanwhile, the cytotoxicity could pass the test standard of biocompatibility.

Table 2

Note 1: In Vitro Cytotoxicity Test

The cell proliferation rate is detected according to the standard in EN ISO 10993-5: 2009 biological evaluation of Medical Devices Part 5: Tests for in vitro cytotoxicity. The test of in vitro cytotoxicity of cross-linked sodium hyaluronate is performed as Class III medical devices.

Specific detection methods are as follows:

① Mix the cross-linked sodium hyaluronate gel to be tested with RPMI1640 medium according to 0.2 g/ml, and place them at 37° C., 5% carbon dioxide incubator for extraction 72 hours, filter through 0.22 μm millipore membrane for sterilization, to get the extract liquid;

② Inoculate $1 \times 10^5$/mL L929 cell suspension in 96-well cell culture plates, place them at 37° C. carbon dioxide incubator for 24 hours. When cells grow attached to the wall, remove the supernatant, and divide into the control group and experimental group;

TABLE 1

| | The weight ratio of | Feeding Quantity | | |
|---|---|---|---|---|
| Example | sodium hyaluronate:BDDE:1, 2-epoxy dodecane | sodium hyaluronate, g | 1,4-butanediol diglycidyl ether (BDDE), ml | 1,2-epoxy dodecane, ml |
| 1 | 10:2:1 | 10 | 1.0 | 0.5 |
| 2 | 10:2:0 | 10 | 1.0 | 0 |
| 3 | 10:0:1 | 10 | 0 | 0.5 |
| 4 | 10:3:0 | 10 | 1.5 | 0 |
| 5 | 10:3:1 | 10 | 1.5 | 0.5 |
| 6 | 10:3:2 | 10 | 1.5 | 1.0 |
| 7 | 10:4:0 | 10 | 2.0 | 0 |

The particle size, injectability, cytotoxicity, enzymatic degradation rate and swelling degree of gel prepared in Examples 1-7 are detected; at the same time, the commercial BDDE-cross-linked sodium hyaluronate gel is detected. The detection results are shown in Table 2.

③ add RPMI1640 medium to the control group; and add RPMI1640 medium containing 50% of above extract liquid in the experimental group. Place the control group and the experimental group to 37° C. carbon dioxide incubator for continuous culture. Take them out 2 days later, add 20 μL of

TABLE 2

| Gel | Example 1 | Example 2 | Example 3 | Example 4 | Example 5 | Example 6 | Example 7 | Commercial product crosslinked by BDDE |
|---|---|---|---|---|---|---|---|---|
| Particle size (microns) | 250 | 300 | Clustered gel | 280 | 300 | 180 | 200 | 350 |
| Injectability (30G needle) | Easy | Easy | Easy | Easy | Easy | Easy | Difficult | Easy (containing lubricant) |
| Cytotoxicity, grade (RCR %) | Grade 1 (90.0) | Grade 1 (83.84) | Grade 1 (95.0) | Grade 1 (82.2) | Grade 1 (85.4) | Grade 1 (76.2) | Grade 2 (65.0) | Grade 1 (85.2) |
| Enzymatic degradation rate (%) | 20.0 | 53.0 | 80.0 | 40.3 | 15.0 | 10.0 | 35.0 | 86.0 |
| Degree of swelling (%) | 3500 | 2500 | 7450 | 2100 | 2600 | 2400 | 1500 | 2200 |

As shown from table 2, by adding the quantity of BDDE cross-linking agent alone (in examples 2, 4, 7), the degree of swelling would decrease, and the resistance to enzymolysis MTT solution (5 mg/ml) in each well of the culture plate, continue to culture 4 hours at 37° C., and then terminate the culture;

④ Carefully draw the culture supernatant in the well, and add 200 μL DMSO to each well. After shaking 10 min and mixing well, measure the absorbance value using ELISA Analyzer at 630 nm, respectively;

⑤ Calculate the RCR of cells according to the formula: RCR (%)=(the average absorbance value of the experimental group/the average absorbance value of the control group)×100%;

⑥ The relationship between RCR and cytotoxicity grading is as follows:
RCR is not less than 100%, cytotoxicity grade of 0;
RCR is 75~99%, cytotoxicity grade of 1;
RCR is 50~74%, cytotoxicity grade of 2;
RCR is 25~49%, cytotoxicity grade of 3;
RCR is 1~24%, cytotoxicity grade of 4;
RCR is 0%, cytotoxicity grade of 5;
The biocompatibility of cross-linked sodium hyaluronate gel can be judged using the RCR determined by the above method. The higher the RCR, the better the biocompatibility of cross-linked sodium hyaluronate gel to be tested;

Table 2
Note 2 Enzymatic Degradation Rate
Specific detection procedures are as follows:
① Take the cross-linked sodium hyaluronate gel sample to be tested and dilute it to the concentration of cross-linked sodium hyaluronate at 4 mg/ml using PBS, which is used as the test solution;
② Take 1.0 g test solution and add 50 U 1 ml hyaluronidase solution for shaking 1 min, and water bath for 24 hours at 37° C., and then boiled 10 min for inactivation at 100° C.;
③ Filter the filtrate through a 0.45 μm microporous membrane and then set the volume to 10 ml with PBS;
④ Determine the content of uronic acid using the modified carbazole spectrophotometric method (reference: Bitter. T, Muir UM, (1962) A modified uronic acid carbarbazole reation. Anal. Biochem. 4, 330-333.), multiplied by 2.07 to convert to the content of cross-linked sodium hyaluronate ($C_1$) in the sample solution added with enzyme solution; the content of cross-linked sodium hyaluronate in the sample without added with enzyme solution is $C_2$. Calculate the enzymatic degradation rate=$C_1/C_2$×100%;

The resistance to enzymolysis of cross-linked sodium hyaluronate gel is judged according to the enzymatic degradation rate determined according to the above method. The lower the enzymatic degradation rate, the better the resistance to enzymolysis of cross-linked sodium hyaluronate gel; and the longer the in vivo retention time of cross-linked sodium hyaluronate gel, the better the long-acting stability of the gel.

Table 2
Note 3 Degree of Swelling
Specific detection procedures are as follows:
Dry the gel in vacuum condition after membrane forming to get the gel membrane, and accurately weigh it (Wd), and add it to PBS, place it under room temperature 24 hours. Take out the fully-expanded gel membrane. After removing the free water on the surface of gel membrane using absorbent paper, weigh the gel membrane (Wg), and calculate the degree of swelling (%)=(Wg/Wd)×100%;

The injectability of cross-linked sodium hyaluronate gel can be judged indirectly according to the degree of swelling measured above. The higher the degree of swelling, the better the hydrophily of the cross-linked sodium hyaluronate gel to be tested; the softer the gel, the better the injectability of gel.

Table 2
Note 4 Gel Particle Size
Specific Method:
The particle size (D) is measured by Mastersizer 2000 Particle Size Analyzer produced by Malvern, UK [4,3].

Table 2
Note 5 Injectability
Specific detection methods are as follows:
Load the sterilized gel in a 1 ml disposable sterile syringe, and install 30G injection needle, and then squeeze out the gel according to the normal injection extrusion method. Judge the difficulty of injectability by hand feeling.

Examples 8~9

The method for preparing cross-linked sodium hyaluronate gel in this Example is basically the same as that in Example 1, with the difference that the molecular weight of sodium hyaluronate is 1,500,000 and the weight ratio of sodium hyaluronate:BDDE: 1,2-epoxy dodecane is 10:3:1 and 10:3:2, respectively.

Measure the enzymatic degradation rate of gel prepared in above Examples 8-9 according to the above method, and the results are 30.20% and 32.5%, respectively, suggesting that the requirements for resistance to enzymolysis can be met when the molecular weight of sodium hyaluronate is 1,500,000 and the weight ratio of sodium hyaluronate:BDDE:1, 2-epoxy dodecane is 10:3:1.

Figure 2:
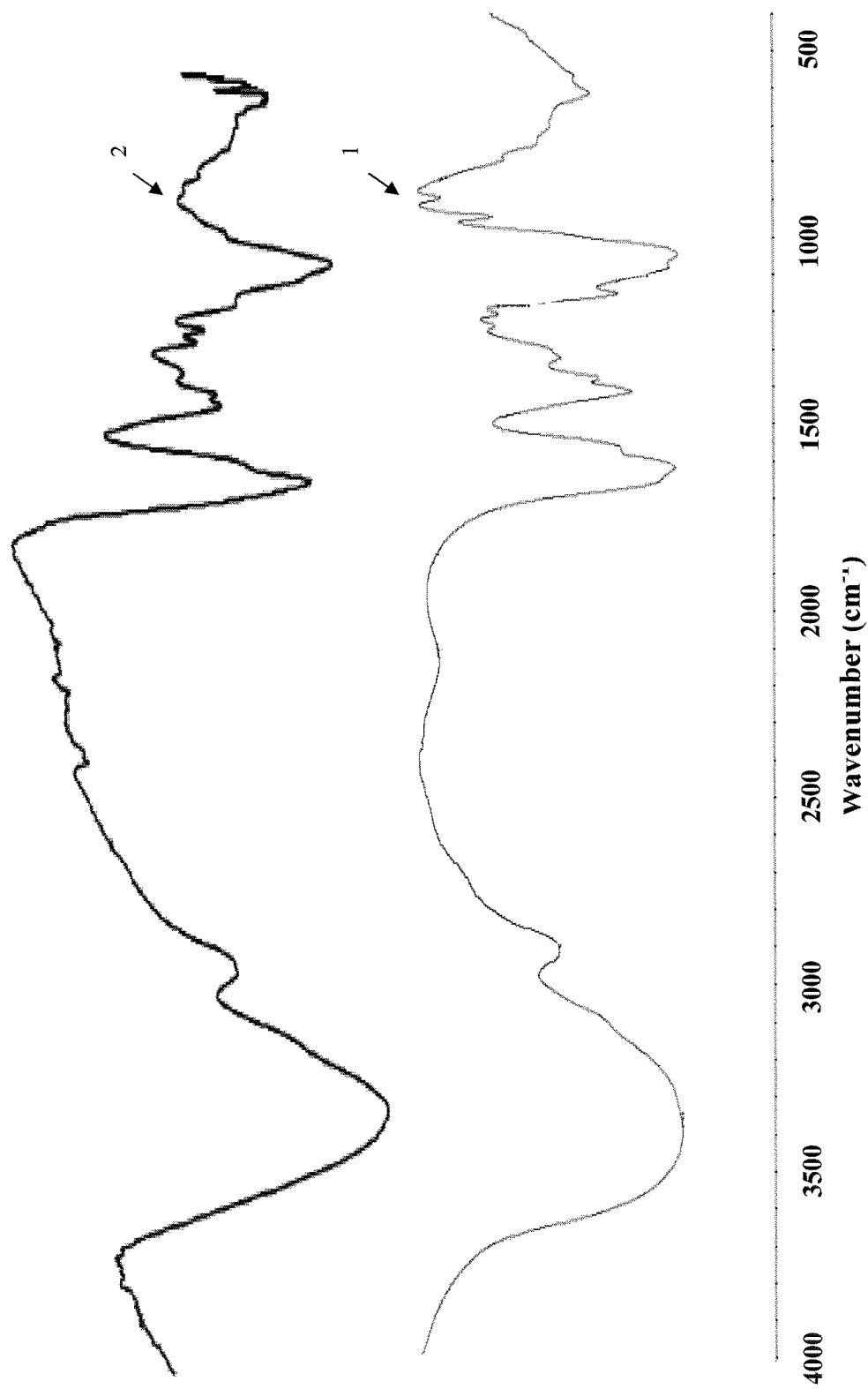
FIG. 2 is a FT-IR spectrum

Infrared Spectrum Detection of Cross-Linked Sodium Hyaluronate Gel in the Present Invention
① Using the conventional FT-IR Fourier transform infrared spectrometer
② Detection method is as follows:
The infrared structures of raw material sodium hyaluronate, cross-linked sodium hyaluronate gel freeze-dried sample prepared in the Example 1 and potassium bromide pellet were scanned and detected on a FT-IR using the conventional method, to get the spectra as shown in FIG. 2, of which, 1 is the FT-IR spectrum of raw material sodium hyaluronate; 2 is the FT-IR spectrum of cross-linked sodium hyaluronate gel;

Through analysis on spectra 1 and 2 in FIG. 2, the spectra of their infrared structures are the same, having the following peaks: 3395 $cm^{-1}$ [ν (NH), ν (OH) OH and NHCO], 2916 $cm^{-1}$ [ν (CH) C—CH2-C], 1615 $cm^{-1}$ [δ (NH) amide (II) and carboxylic acid group], 1411 $cm^{-1}$ [ν (CN) and 6 (NH) amide III], 1377 $cm^{-1}$ [ν (C=O)—COOH], 1044 $cm^{-1}$ [ν (C—O)C—O—C], 945 $cm^{-1}$ [6 (O—H) and ν (C—C)C—O—C(ring) and OH], 612 $cm^{-1}$ [ω (N—H) amide I], demonstrating that cross-linking modification of sodium hyaluronate in the present invention does not change the basic chemical structure of sodium hyaluronate, thus ensuring that the biocompatibility of cross-linked sodium hyaluronate gel is not affected.

$^1$H-NMR Analysis on Cross-Linked Sodium Hyaluronate Gel in the Present Invention
Detection Method
① NMR instrument (300 HZ, Bruker, Switzerland); ② Detection method is as follows:
1) Dissolve the raw material sodium hyaluronate in $D_2O$ and conduct NMR detection. The detection spectrum is shown in FIG. 3;
2) Adjust cross-linked sodium hyaluronate gel (prepared in Example 1) to pH=8 using NaOH, sterilize it at 121° C., high pressure condition for 30 min to form liquid, and then it is freeze-dried to obtain the powder, and dissolved in $D_2O$/DMSO for NMR detection. The detection spectrum is shown in FIG. 6;

3) Prepare the sodium hyaluronate treated with long-chain alkane containing epoxy group alone and the sodium hyaluronate crosslinked with 1,4-butanediol diglycidyl ether alone, respectively, adjust their pH to 8 with NaOH solution, and sterilize them at 121° C., high pressure condition for 30 min to form liquid, and then freeze-dried to obtain the powder, and dissolved in $D_2O$/DMSO for NMR detection. The detection spectra are shown in FIG. 4 and FIG. 5;

In $^1$H-NMR spectrum in the FIG. 3, the position of acetamide group N-Acetyl ($NHCOCH_3$) of sodium hyaluronate is at 1.9~2.2 ppm, the position of glucuronic acid (10H) is at 3.0~4.0 ppm and the position of glucose unit anomeric hydrocarbon (2H) is at 4.35~4.45 ppm;

In $^1$H-NMR spectrum in the FIG. 4, peaks appear in the positions 1.2~1.4 ppm and 0.65~0.85 ppm in addition to the above peaks in FIG. 3, which represent methylene $CH_2$ peak and long chain C-terminal group $CH_3$ respectively, demonstrating that chemical bonding between long-chain alkane containing epoxy group and sodium hyaluronate can be achieved in the present invention;

In $^1$H-NMR spectrum in the FIG. 5, in addition to above peaks in FIG. 3, the peak of O—$CH_2CH_2$ appears in the position 1.5~1.7 ppm, which represents the crosslink bond between cross-linking agent BDDE and sodium hyaluronate, demonstrating that the BDDE cross-linking agent containing epoxy group) can be crosslinked with sodium hyaluronate;

In $^1$H-NMR spectrum in the FIG. 6, in addition to above peaks in FIG. 3, three peaks appear simultaneously:long-chain C-terminal $CH_3$ that represents long-chain alkane containing epoxy group appearing at 0.65~0.85 ppm, methylene $CH_2$ that represents alkylene oxide appearing at 1.2~1.4 ppm, and the crosslink bond O—$CH_2CH_2$ that represents BDDE and sodium hyaluronate at 1.5~1.7 ppm, demonstrating that, the method preparing the cross-linked sodium hyaluronate gel in the present invention can guarantee the crosslinking between cross-linking agent containing epoxy group of 1,4-butanediol diglycidyl ether (BDDE) and sodium hyaluronate, and guarantee the chemical bonding between 1,2-epoxy dodecane and sodium hyaluronate.

When the polyethylene glycol diglycidyl ether with molecular weight of 500~6000, 1,2,7,8-diepoxyoctane or 1,2,3,4-diepoxybutane, as the cross-linking agents containing epoxy group, react with long-chain alkane containing epoxy group (6~18 carbon atoms of long-chain alkanes), the same performance of cross-linked sodium hyaluronate gel can be obtained. It is not described in details herein.

What is claimed is:

1. A method for preparing a cross-linked sodium hyaluronate gel for tissue filler suitable for plastic surgery, consisting of:
   ① dissolving a dry powder of sodium hyaluronate in a mixture of 0.2~0.5M aqueous sodium hydroxide solution and dimethyl sulfoxide to produce an alkaline solution of sodium hyaluronate, and then adding a long-chain alkane containing a single epoxy group and a cross-linking agent containing an epoxy group, heating the alkaline solution of sodium hyaluronate to 35° C.~50° C. with stirring for 2~5 hours to produce a product solution, cooling the product solution down to room temperature; then adding acetone dropwise while stirring to form a solid-liquid mixture, adding hydrochloric acid to adjust the pH value of the solid-liquid mixture to 6.5~7.4, filtering the solid-liquid mixture and collecting a solid material, which is washed 3~5 times using isopropanol and acetone, respectively, and then drying the solid material under vacuum until a content of a volatile matter is lower than 2 ppm to produce a cross-linked sodium hyaluronate powder; wherein a weight ratio of sodium hyaluronate:the cross-linking agent containing an epoxy group:the long-chain alkane containing a single epoxy group is 10:4~1:1~4; a number of carbon atoms in the long-chain alkane containing the epoxy group is 6~18; a volume ratio of 0.2-0.5M sodium hydroxide solution to dimethyl sulfoxide is 10:7~1; a concentration of sodium hyaluronate is 4 wt % to 8 wt % in the sodium hyaluronate alkaline solution; a volume ratio of the sodium hydroxide solution to acetone added dropwise is 1:4~2:3; an average molecular weight of sodium hyaluronate is 500,000~2,000,000 Da; the cross-linking agent containing an epoxy group is one of the following: 1,4-butanediol diglycidyl ether, polyethylene glycol diglycidyl ether with a molecular weight of 500~6,000, 1,2,7,8-diepoxyoctane, or 1,2,3,4-diepoxybutane;
   ② adding water to the cross-linked sodium hyaluronate powder obtained in step ① to form a cross-linked sodium hyaluronate gel; collecting gel particles, which are washed with water while stirring for 2~5 hours at 15° C.~35° C., followed by filtration to collect the gel particles, and repeating water washing 4~5 times, and then collecting the gel particles;
   ③ adding isotonic saline to the gel particles collected in step ②; after stirring for 2~5 hours at 15° C.~35° C. collecting the gel particles by filtration, followed by washing with isotonic saline, repeating isotonic saline washing 4~5 times, and then collecting gel particles with an average particle size of 150 μm-350 μm by screen sieving; and
   ④ filling a pre-sterilized disposable syringe with the gel particles collected in step ③, and sterilizing the filled syringe by steam at 121° C.~125° C. for 15~25 min to produce the cross-linked sodium hyaluronate gel for tissue filler suitable for plastic surgery.

2. The method for preparing the cross-linked sodium hyaluronate gel according to claim 1, wherein the cross-linked sodium hyaluronate gel contains chemically bonded hydrophobic groups having a self-adhesive self-aggregating property.

* * * * *